United States Patent [19]

Chu et al.

[11] 4,305,878
[45] Dec. 15, 1981

[54] PURIFYING ETHYL TETRAHYDROFURFURYL ETHER BY AQUEOUS SALT EXTRACTION

[75] Inventors: Arthur S. Chu, E. Amherst; Frank Scarcello, Westfalls; Emil J. Walerko, Blasdell, all of N.Y.

[73] Assignee: Allied Corporation, Morris Township, Morris County, N.J.

[21] Appl. No.: 225,289

[22] Filed: Jan. 15, 1981

[51] Int. Cl.$^3$ ............................................. C07D 307/12
[52] U.S. Cl. .................................................. 260/347.8
[58] Field of Search ..................................... 260/347.8

[56] References Cited

U.S. PATENT DOCUMENTS 2,153,135  4/1939  Dickey et al. ............... 260/347.8 Y
3,940,502  2/1976  Winter ......................... 260/347.8 X

*Primary Examiner*—Richard Raymond
*Attorney, Agent, or Firm*—Alan M. Doernberg; Jay P. Friedenson

[57] ABSTRACT

Mixtures including ethyl tetrahydrofurfuryl ether (ETFE), tetrahydrofurfuryl alcohol (THFA), ethanol and water, and usually also an ethyl halide, are extracted with an aqueous solution of an alkali metal or alkaline earth metal chloride salt until THFA/ETFE ratios below 0.01 or 0.001 are achieved. Thereby THFA and ethanol, each of which are difficult to separate from ETFE by distillation, are removed.

5 Claims, No Drawings

PURIFYING ETHYL TETRAHYDROFURFURYL ETHER BY AQUEOUS SALT EXTRACTION

BACKGROUND OF THE INVENTION

The present invention relates to the purification of ethyl tetrahydrofurfuryl ether (ETFE) from mixtures thereof with tetrahydrofurfuryl alcohol (THFA) and ethanol such as are formed by reaction of THFA, ethyl chloride and sodium hydroxide or sodium.

Processes to produce ETFE from THFA involving THFA have been described and generally result in a crude product including ETFE, THFA, ethanol and frequently also an ethyl halide such as ethyl chloride. Attempts to distill the mixture to produce high quality, dry ETFE have failed to produce high quality material suitable for refrigeration applications even though ETFE and THFA differ in their boiling points by 21° C., and ethanol and ETFE differ in their boiling points by 79° C.

Accordingly, the present invention is designed to purify ETFE of THFA and ethanol. It should be understood that other impurities such as ethyl halide and water can be removed later by distillation or other means.

BRIEF DESCRIPTION OF THE INVENTION

The present invention includes a method of recovering ethyl tetrahydrofurfuryl ether (ETFE) from mixtures which comprises the steps:

(a) mixing an aqueous solution of an alkali metal or alkaline earth metal chloride salt with a mixture comprising ETFE, tetrahydrofurfuryl alcohol, ethanol and water, (b) separating an aqueous phase from an organic phase with the organic phase containing more ETFE, less tetrahydrofurfuryl alcohol and less ethanol than the mixture, and (c) repeating steps (a) and (b) with the organic phase of each step (b) used as the mixture for each subsequent step (a) until the organic phase contains an impurity level of tetrahydrofurfuryl alcohol by weight of ETFE no greater than 0.01.

DETAILED DESCRIPTION OF THE INVENTION

The method of the invention involves purifying ETFE from impurities by repeated extraction with an aqueous salt solution. The impurities present in crude ETFE include THFA, ethanol and water, and may further include an ethyl halide such as ethyl chloride. The present extraction process removes both THFA and ethanol, but may not remove other impurities. It is the THFA and ethanol, however, which are difficult to separate from ETFE by distillation.

The salt used for the aqueous solution may be any alkali metal or alkaline earth metal chloride such as lithium chloride, sodium chloride, potassium chlorate, barium chloride, calcium chloride, magnesium chloride or the like. Sodium and calcium chloride are most preferred, with potassium chloride being next. Concentrations from low levels up to the solubility limit in water may be used, with reasonably concentrated solutions being preferred. Most preferred is aqueous sodium chloride at least 20 weight percent NaCl.

The precise temperatures and volume ratios of aqueous to organic in each extraction are not critical, so long as freezing and boiling of water or organics and salting out of salts are avoided. Room temperature or temperatures up to 70° C. are preferred. Mixing ratios from 10:1 to 1:10 are preferred. The extractions may be conducted in any conventional equipment for liquid-liquid extraction and may proceed in separate stages or continuously as by countercurrent flow through a column.

It is preferred that the extraction be conducted until the THFA/ETFE ratio falls below 0.01, more preferably below 0.001. THFA removal is a function of the number of extraction stages used. Based on the data for countercurrent extractions in Examples 7–14, the THFA/ETFE ratio can be reduced to 0.0005 with 22 stages and to 0.0003 with 16 stages. Less stages are required on a batch basis with fresh aqueous solutions for each extraction. Thereafter, the organic layer can be fractionally distilled or scrubbed with an absorbent to separate pure ETFE from other impurities (e.g ethyl chloride) and any dissolved water. Since water is an impurity most deleterious to the stability of ETFE-refrigerant mixtures (see U.S. Pat. No. 4,072,027 issued Feb. 7, 1978), the effectiveness of aqueous solutions for purification is considered to be surprising.

EXAMPLE 1

A crude mixture (100 g) containing 76% ETFE, 21% tetrahydrofurfuryl alcohol and 3% of various impurities including ethanol was mixed with 40 g of a saturated calcium chloride solutions at room temperature. After settling, a 68 g aqueous layer was removed. When these steps were repeated two more times with 40 g saturated calcium chloride solutions, 50 g and 44 g of aqueous solutions were removed. The remaining 68 g organic solution was analyzed by gas chromatography and appeared to contain about 96.6% ETFE and about 0.25% tetrahydrofurfuryl alcohol or about 0.26% THFA/ETFE. A mass balance showed 220 g in and 230 g out, such that some error was present.

EXAMPLE 2

The crude mixture (150 g) used in Example 1 was extracted three times with 60 g aqueous sodium chloride solutions to produce aqueous phases of 66 g, 71 g and 68 g. The remaining 130 g organic phase was analyzed by gas chromatography and appeared to contain 89.4% ETFE and 9.2% THFA. Further extractions would be required to achieve the desired purity levels.

EXAMPLE 3

13.43 weight units of the crude mixture used in Example 1 was mixed with 4 weight units of water and 2.6 weight units of calcium chloride, agitated for 15 minutes and allowed to settle for 30 minutes. Small samples were taken of the organic phase (under 0.01 weight units) and the remainder of the organic phase was again extracted with 4 weight units water and 2.6 weight units of calcium chloride. The aqueous phases produced were 9.4 weight units, 7.7 weight units, 7.0 and 6.9 weight units. The final organic phase was 9.1 weight units. The original organic phase and the first two samples were analyzed by gas chromatography and showed the following by area percentages:

|      | 0    | 1    | 2    |
|------|------|------|------|
| ETFE | 76.0 | 91.6 | 96.5 |
| THFA | 21.1 | 6.4  | 1.8  |

EXAMPLE 4

A different crude mixture (175 g) having the ingredients indicated in Table I under "0" was extracted five times with 70 g of 37.5% aqueous calcium chloride at 25° C. Samples (2 g) of the organic layer were taken after each extraction except the first for analysis, with results as indicated in Table I.

TABLE I

| Extraction Component | 0 | 2 | 3 | 4 | 5 |
|---|---|---|---|---|---|
| Ethyl Chloride | 2.20 | 2.55 | 2.63 | 2.55 | 2.42 |
| Ethanol | 0.83 | 0.47 | 0.27 | 0.21 | 0.34 |
| ETFE | 72.5 | 93.6 | 95.6 | 96.3 | 96.9 |
| THFA | 23.7 | 2.75 | 0.89 | 0.24 | 0.06 |
| LB | 0.04 | 0.08 | 0.07 | 0.12 | 0.09 |
| IMP | 0.54 | 0.53 | 0.51 | 0.53 | 0.48 |
| HB | — | 0.003 | 0.007 | 0.026 | 0.031 |

LB = low boilers (under 153° C.)
HB = high boilers (over 178° C.)
IMP = other impurities between 153° C. and 178° C.

It apperars that a THFA/ETFA ratio below 0.01 was achieved by the third extraction, below 0.003% by the fourth extraction and below 0.001% by the fifth extraction.

EXAMPLE 5

Using a still different batch of crude mixture (250 g) having the analysis by gas chromatography indicated in Table 2 under the heading "0" fourteen extractions were performed with 24% aqueous NaCl using aqueous charges starting at 100 g for the first cycle and declining 1 g each cycle to 91 g on the eleventh cycle (to compensate for sampling, both the fourth and fifth cycles used 97 g) and thereafter 83 g for the twelth and thirteenth cycles and 80 g for the fourteenth cycle. Organic samples after the fifth, tenth and fourteenth cycles were analyzed by gas chromatography, giving the results shown in Table 2.

TABLE II

| Extraction Component | 0 | 5 | 10 | 14 |
|---|---|---|---|---|
| Ethyl Chloride | 4.07 | 3.23 | 2.77 | 0.02 |
| Ethanol | 0.90 | — | — | 0.03 |
| ETFE | 73.3 | 92.1 | 96.1 | 98.1 |
| THFA | 20.4 | 3.62 | 0.24 | 0.03 |
| LB | 0.05 | — | 0.09 | 0.32 |
| IMP | 0.63 | 0.92 | 0.82 | 1.36 |
| HB | 0.10 | — | — | 0.12 |

It appears from this data that, on a batch basis, THFA/ETFE ratios below 0.003 were achieved by the tenth extraction and below 0.0005 were achieved by the fourteenth extraction.

EXAMPLE 6

Example 4 was repeated extracting 1.4 weight units of the same crude mixture seven times at 55° C. with 57.5% CaCl (7.2 weight units for the first extraction, 5.86 weight units for each subsequent extraction), with samples taken of each organic layer and analyzed as shown in Table 3.

TABLE 3

| | 0 | 1 | 2 | 3 | 4 | 5 | 6 | 7 |
|---|---|---|---|---|---|---|---|---|
| EtCl | 2.20 | 1.54 | 1.36 | 1.13 | 0.90 | 0.65 | 0.58 | 0.58 |
| EtOH | 0.83 | 1.13 | 0.84 | 0.62 | 0.44 | 0.35 | 0.24 | 0.17 |
| ETFE | 72.5 | 88.0 | 93.1 | 95.0 | 96.3 | 96.9 | 97.3 | 97.6 |
| THFA | 23.7 | 7.9 | 3.2 | 1.6 | 0.72 | 0.35 | 0.15 | 0.08 |
| LB* | 0.043 | 0.069 | 0.83 | 0.91 | 0.79 | 0.81 | 0.90 | 0.85 |
| IMP | 0.54 | 0.72 | 0.74 | 0.69 | 0.72 | 0.73 | 0.66 | 0.65 |
| HB | — | 0.007 | 0.01 | 0.03 | 0.01 | 0.02 | 0.02 | 0.09 |

*including ethane at 0.0012-0.0043 area %. These results show THFA/ETFE ratios below 0.01 by the fourth extraction, below 0.005 by the fifth extraction and below 0.002 by the sixth extraction.

EXAMPLES 7-14

Eight runs were made continuously feeding a crude mixture containing 72.7% ETFE, 23.3% THFA, 2.3% ethyl chloride, 0.9% ethanol and 0.8% other impurities to a York-Schieber agitated extraction column with feed points corresponding to 16 and 22 stages. The aqueous feed was 18-20% sodium chloride solution. Different aqueous/organic feed ratios were used between 1.10:1.0 and 0.75:1.0 (by weight). Sodium chloride is the preferred aqueous feed as the soluble fractions of ETFE and THFA in the aqueous effluent can be recovered through distillation. While calcium chloride solution is a more efficient extraction agent, the calcium chloride reacts to form a solid complex in the absence of water in the distillation column reboiler. This prevents residual ETFE and THFA recovery, and aqueous effluent cleaning.

In general, the product organic leaving the extraction column contained a THFA/ETFE ratio below 0.0005 and an ethanol/ETFE ratio below 0.0005 using 22 trays and 20% NaCl solution. Using less trays caused higher THFA and ethanol levels in the product, as exhibited in two examples. Two other examples showed effects due to low NaCl concentration. The density difference between organic and aqueous feeds became small enough to cause organic entrainment in the aqueous effluent stream.

To achieve a desired ETFE product purity, a combination of sufficient contact time in the 22 tray column with a NaCl concentration of at least 20 weight percent was needed.

What is claimed is:
1. A method of recovering ethyl tetrahydrofurfuryl ether (ETFE) from mixtures which comprises the steps:
   (a) mixing an aqueous solution of an alkali metal or alkaline earth metal chloride salt with a mixture comprising ETFE, tetrahydrofurfuryl alcohol, ethanol and water,
   (b) separating an aqueous phase from an organic phase with the organic phase containing more ETFE, less tetrahydrofurfuryl alcohol and less ethanol than the mixture, and
   (c) repeating steps (a) and (b) with the organic phase of each step (b) used as the mixture for each subsequent step (a) until the organic phase contains an impurity level of tetrahydrofurfuryl alcohol by weight of ETFE no greater than 0.01.
2. The process of claim 1 wherein said salt is calcium chloride.
3. The process of claim 1 wherein said salt sodium chloride.
4. The process of claim 3 wherein said aqueous solution is at least 20 weight percent NaCl.
5. The process of claim 1 or 2 or 3 or 4 wherein said impurity level is no greater than 0.001.

* * * * *